United States Patent [19]

Stoy

[11] Patent Number: 5,939,208
[45] Date of Patent: Aug. 17, 1999

[54] METHOD FOR CREATION OF BIOMIMETIC SURFACES

[75] Inventor: Patrick Stoy, Princeton, N.J.

[73] Assignee: Biomimetics, Inc., Rocky Hill, N.J.

[21] Appl. No.: 08/966,343

[22] Filed: Nov. 7, 1997

[51] Int. Cl.⁶ .............................. B32B 27/30; B05D 3/10; C08J 7/12
[52] U.S. Cl. .................... 428/500; 424/422; 424/423; 424/427; 424/487; 427/2.12; 427/2.13; 427/2.24; 427/2.28; 427/2.3; 427/353; 427/352; 427/340; 428/424.2; 428/424.7; 523/103; 523/105; 523/106; 523/108
[58] Field of Search ..................... 427/337, 336, 427/352, 353, 2.24, 2.3, 414, 2.28, 2.1, 2.12, 2.13, 333, 340; 428/500, 424.2, 424.7; 523/103, 105, 106, 108; 424/422, 423, 427, 487

[56] References Cited

U.S. PATENT DOCUMENTS

| | | | |
|---|---|---|---|
| 3,895,169 | 7/1975 | Wichterle | 428/522 |
| 4,587,284 | 5/1986 | Luissi et al. | 524/17 |
| 4,921,497 | 5/1990 | Sulc et al. | 623/6 |
| 4,943,618 | 7/1990 | Stoy et al. | 525/340 |
| 5,120,413 | 6/1992 | Chen et al. | 204/180.1 |
| 5,217,026 | 6/1993 | Stoy et al. | 128/772 |
| 5,274,038 | 12/1993 | Gupta | 515/100 |
| 5,300,635 | 4/1994 | Macfarlane | 536/25.4 |
| 5,319,023 | 6/1994 | Gupta | 525/100 |
| 5,511,547 | 4/1996 | Markle et al. | 128/633 |
| 5,583,213 | 12/1996 | Yafuso et al. | 536/55.3 |
| 5,728,822 | 3/1998 | Macfarlane | 536/25.41 |

OTHER PUBLICATIONS

Anthony G. Gristina: "Biomaterial–Centered Infection: Microbial Adhesion Versus Tissue Integration", Science, (1987) vol. 237 pp. 1588–1595 (no month).

Karel Smetana, Jr. et al: "Macrophage Recognition of Polymers; Effect of Carboxylate Groups", Journal of Materials Science: Materials in Medicine 4 (no month) (1993) pp. 526–529.

Karel Smetana, Jr. et al: "The Influence of Hydrogel Functional Groups on Cell Behavior", Journal of Biomedical Materials Research vol. 24 (no month) (1990) pp. 463–470.

Karel Smetana, Jr. et al: "Artificial Mineralization in Vitro—A Model of Tissue Mineralization, Folia Biologica (Praha), vol. 39, 1993 (no month).

Karel Smetana, Jr.: "Cell Biology of Hydrogels", Biomaterials (1993) vol. 14; No. 14 pp. 1046–1050 (no month).

Karel Smetana, Jr. et al: "The Influence of Chemical Functional Groups on Implant Biocompatibility":, Clinical Materials (1993) pp. 47–49 (no month).

Karel Smetana, Jr. et al: "Intraocular Biocompatibility of Hydroxyethyl Methacrylate and Methacrylic Acid Copolymer/ Partially Hydrolyzed Poly(2–Hydrox–ethyl Methacrylate)", Journal of Biomedical Materials Research (1987) vol. 21 pp. 1247–1253 (no month).

Stanislav Sevcik et al: "Surface Alkaline Hydrolysis of 2–Hydroxyethyl Methacrylate Gels" Journal of Materials Science: Materials in Medicine 6 (1995) pp. 505–509. (no month).

*Primary Examiner*—Diana Dudash
*Attorney, Agent, or Firm*—Kenneth P. Glynn, Esq.

[57] ABSTRACT

In the present invention method, the surface of articles made of acrylic polymers and methacrylic polymers are converted into thin biomimetic layers by using the process involving at least the following two steps:

(a) The polymer surface is contacted, in the presence of water and for a predetermined reaction time necessary to form a continuous surface layer thinner than about 500 microns, with a solution containing one or more tetraalkylammonium hydroxides of the general formula:

$$R_1R_2R_3R_4N^+OH^-$$

where $R_1$, $R_2$, $R_3$, $R_4$ are the alkyl substituents, in which the sum of the number of carbon atoms is equal to or larger than 8 but smaller than 45; and, (b) The article is removed from the aqueous reaction solution and excess of tetraalkylammonium hydroxide is removed from the polymer surface by washing the polymer with a liquid miscible with the tetraalkylammonium hydroxide.

20 Claims, No Drawings

METHOD FOR CREATION OF BIOMIMETIC SURFACES

BACKGROUND OF THE INVENTION

1. Field of the Invention

The present invention relates to articles formed primary of polymers selected from acrylic polymers, methacrylic polymers, copolymers and mixtures of these, with modified surface characteristics to create biomimetic products. More specifically, the invention involves the method of making such articles and the products resulting from that method.

2. Information Disclosure Statement

Hydrophobic plastics, such as silicone rubber, polymethylmethacrylate, polyethylene or polyvinylchloride are often used in medical devices (e.g., as catheters, stents or implants) and are exposed to contact with tissues or body fluids.

One of the problems with the use of these materials in device applications is their interaction with proteins. Proteins from body fluids are rapidly and irreversibly adsorbed onto the hydrophobic surfaces. The strongly bound proteins can denature and initiate an autoimmune reaction. Moreover, the deposited protein layer conditions the surface for subsequent cell attachment, including bacterial adhesion. The proteins, cells and microorganisms form a "biofilm" on the hydrophobic surface that is a source of potential problems, such as a bacterial colonization and the consequent risk of material-centered infections and seeded infections that are dangerous and difficult to treat. See Anthony G. Gristina: "Biomaterial-Centered Infection: Microbial Adhesion Versus Tissue Integration", *Science*, (1987) Volume 237, pages 1588 through 1595. In addition, such surfaces are recognized by the immune system as foreign, causing foreign body reactions during which leukocytes, such as macrophages, attempt to surround and eliminate the invader.

Hydrogels were considered an answer to this problem since they do not adsorb proteins as strongly as hydrophobic plastics or metals. However, this turned out to be only partly true. Although largely hydrophilic, most hydrogels do contain some hydrophobic domains which bind protein in much the same way as hydrophobic plastics. Thus, hydrogels differ from other plastics quantitatively rather than qualitatively (i.e., less protein is adsorbed on the hydrogel surface, but at least part of the adsorbed protein is bound by the same strong hydrophobic interactions that are responsible for the complications in hydrophobic plastics).

Moreover, most hydrogel surfaces are recognized by the immune system as foreign bodies, causing long-term irritation and sterile inflammation. It has been found by Smetana and others that the presence of anionic carboxylate groups on the surface of an implanted hydrogel will reduce or prevent protein adsorption, see Karel Smetana, Jr., Jiri Vacik, M. Houska, Dana Souckova, Jaromir Lukas "Macrophage Recognition of Polymers; Effect of Carboxylate Groups", *Journal of Materials Science: Materials in Medicine* 4 (1993), pages 526 through 529, prevent attachment and spreading of many cells and prevent recognition of the hydrogel by macrophages as a "foreign body", see Karel Smetana, Jr., Jiri Vacik, Dana Souckova, Zuzana Krcova, Jiri Sulc "The Influence of Hydrogel Functional Groups on Cell Behavior", *Journal of Biomedical Materials Research*, Volume 24, (1990) pages 463 through 470. Furthermore, the presence of carboxylate groups delays or prevents calcification of implants, see K. Smetana, Jr., M. Stol and M. Novak: Artificial Mineralization In Vitro—A Model Of Tissue Mineralization, Folia Biologica (Praha), Volume 39, 1993. In Smetana's opinion, the carboxylates are functioning in this manner by masking with their electric charge and their high hydration, various functional groups (hydroxyl, amine, amide or various hydrophobic groups) that could otherwise be loci of interaction with proteins or cell surfaces. In Smetana's view, the surface of a carboxylated hydrogel mimics the charge and high hydration of the surface layer (glycocalyx) of certain cells (such as fetal tissue cells or cells of certain pathogenic bacteria) that are rich in sialic acid and known to be unrecognized by immune system, see Karel Smetana, Jr.: "Cell Biology of Hydrogels", *Biomaterials* (1993), Volume 14; No. 14, pages 1046 through 1050. This biomimetic behavior is valuable for various implants because it can diminish foreign body reaction, improve healing and reduce the risk of post-surgical complications. Consequently, hydrogels with high carboxyl content were synthesized and used for devices like mammary and intraocular lens implants, see Karel Smetana, Jr., Jiri Vacik, Dana Souckova, Sarka Pitrova: "The Influence of Chemical Functional Groups on Implant Biocompatibility", *Clinical Materials* (1993), pages 47 through 49).

High carboxyl content can be achieved in various ways. The most usual method is a crosslinking copolymerization of acrylic or methacrylic acid with less polar monomers such as 2-hydroxyethylmethacrylate (HEMA) or methylmethacrylate. However, the benefit of carboxylate groups is rather limited in this case. A disadvantage of the homogeneous increase of carboxylate content is the increase of overall water content and consequent decrease of some essential hydrogel properties (such as tensile strength, tear strength and refractive index). Therefore, the carboxylate concentration has to be kept low and its benefit is thereby limited. If a more hydrophobic comonomer (such as benzylmethacrylate) is used to compensate for the extreme hydrophilicity of the acrylic or methacrylic acid (so that a higher carboxylate concentration can be achieved), then there is a danger of causing a phase separation resulting in the formation of hydrophobic domains and/or micropores—both very detrimental to biocompatibility.

Carboxylate groups can also be introduced by hydrolysis of acrylic or methacrylic polymers. Hydrogels are preferred substrates for chemical modifications because of the mobility and accessibility of their functional groups. For bulk hydrolysis, the reagents need access to the interior of the substrate so that acid or base-catalyzed hydrolysis is usually carried out on acrylic or methacrylic hydrogels such as PolyHEMA, see Karel Smetana, Jr., Jiri Sulc, Zuzana Krcova, Sarka Pitrova: "Intraocular Biocompatibility of Hydroxyethyl Methacrylate and Methacrylic Acid Copolymer/Partially Hydrolyzed Poly(2-Hydroxyethyl Methacrylate)", *Journal of Biomedical Materials Research* (1987), Volume 21, pages 1247 through 1253, or aquagels such as polyacrylonitrile aquagel, see V. A. Stoy, G. P Stoy and J. Lovy: "Method for Preparing Polyacrylonitrile Copolymers by Heterogeneous Reaction of Polyacrylonitrile Aquagel", U.S. Pat. No. 4,943,618. This method provides better results than copolymerization in two respects—it yields stronger hydrogels for a given carboxyl content, and the material has a more distinct biomimetic behavior.

Notwithstanding the foregoing, the high carboxyl content in the hydrogel bulk limits its useful properties. For that reason, it has been proposed to treat only the surface of a hydrogel. In this way, one can create a surface with high carboxyl content while leaving the hydrogel bulk intact. The main problem is controlling the gradient of carboxyl composition and swelling in the hydrogel substrate. The gradient is controlled by the ratio between the rate of hydrolysis and the rate of diffusion of reagents and/or catalysts to the reaction site. Hydrogels suitable for long-term implants are usually highly permeable to water and low-molecular weight catalysts. At the same time, they have to be considerably stable against hydrolysis. Consequently, it is difficult to find conditions under which the reaction rate is much faster than diffusion, and surface hydrolysis often has to be carried out at extreme conditions that are difficult to control high concentrations of strong acids, see G. Stoy and V. A. Stay, "Guidewires With Lubricious Surface and Method of Their Production", U.S. Pat. No. 5,217,026, or bases, see Stanislav Sevcik, Jiri Vacik, Dana Chmelikova, Karel Smetana, Jr.: "Surface Alkaline Hydrolysis of 2-Hydroxyethyl and Methacrylate Gels" *Journal of Materials Science: Materials in Medicine* 6 (1995), pages 505 through 509, and high temperatures. Even at these conditions, water and catalyst have a tendency to penetrate deep into the hydrogel so that the gradient is shallow and hydrolysis proceeds in the hydrogel bulk as well as on the surface. Change of the bulk properties of the hydrogel is an undesirable complicating factor. In addition, the uncontrolled gradient of composition and swelling causes shape distortion and uneven, wrinkled surfaces. Control of the gradient by reaction kinetics is very difficult. For that reason, attempts were made to control the swelling gradient by running the reaction in a dehydrated state (for instance, in presence of high concentrations of salts that deswell the hydrogel due to the high osmotic pressure in the solution surrounding the hydrogel). However, consistent and controlled surface hydrolysis is difficult under these conditions.

One of the typical hydrogels selected for surface modification is covalently crosslinked poly(2-hydroxyethyl methacrylate) (PHEMA), used in products such as intraocular lenses (IOL). Previous attempts at surface modification of PHEMA IOLs centered around conventional base-catalyzed hydrolysis with NaOH and $Na_2CO_3$. These attempts were not very successful because of the difficulties involved in containing the hydrolysis to the polymer surface. The shallow gradient of hydrolysis using this method resulted in the bulk material composing the lens being hydrolyzed as well as the surface. This increased the lens's swelling, and thus altered its optical properties. The difficulties of this method persisted even if used on pre-dried xerogels with short reaction times. The race between hydrolysis of the surface and diffusion into (and hydrolysis of) the bulk material proved unwinnable with the given catalysts.

In an attempt to contain the hydrolysis to the surface, the PHEMA IOLs were treated in a solution of $H_2SO_4$ and $NaHSO_4$, see Jiri Sulc, Zuzana Krcova: "Method for the Formation of Thin Hydrophilic Layers on the Surface of Objects Made From Non-Hydrophilic Methacrylate and Acrylate Polymers", U.S. Pat. No. 4,921,497. The idea being that the $NaHSO_4$ would suppress the swelling of the lens, decreasing the acid's penetration into and hydrolysis of the bulk material. However, it was not deemed reliable enough for large-scale production. An alternative method used an acid-catalyzed reaction of polyacrylate and polymethacrylate derivatives with a hot (90–120° C.) mixture of concentrated $H_2SO_4$ and glycerol, see Otto Wichterle, U.S. Pat. No. 3,895,169. This reaction involves simultaneous hydrolysis, esterification and reesterification, sulphatation and crosslinking. The complicated reaction kinetics and the very harsh conditions made the process very sensitive and unforgiving, rendering it unsuitable for large-scale production of medical devices. In addition, sulfate groups do not have the same biomimetic effect as the more desirable carboxylate groups.

Hydrophobic plastics, such as polymethylmethacrylate (PMMA), can also in theory be hydrolyzed on the surface, forming a highly carboxylated hydrophilic surface layer. However, owing to autoaccelerating kinetics and increasing diffusion rate with reaction conversion, the surfaces of hydrophobic plastics, such as PMMA, are typically etched or pitted by the hydrolysis rather than covered by a continuous hydrogel layer.

Hydrophobic plastics are often hydrophilized by means of hydrogel coatings. The problems with adhesion of hydrogels to hydrophobic materials prevents the use of coatings with very high content of carboxylate groups. Most of the hydrogels used for coatings have a moderate hydrophilicity and no carboxylate groups. The main problem of coatings-of permanent application of this type is their durability. The hydrophilic moiety in these coatings, such as, polyethylene glycol or phosphoryl choline groups, can be removed by hydrolysis under certain conditions.

SUMMARY OF THE INVENTION

In the present invention method, the surface of articles made of acrylic polymers and methacrylic polymers are converted into thin biomimetic layers by using the process involving at least the following two steps:

(a) The polymer surface is contacted, in the presence of water and for a predetermined reaction time necessary to form a continuous surface layer thinner than about 500 microns, with a solution containing one or more tetraalkylammonium hydroxides of the general formula:

$$R_1R_2R_3R_4N^+OH^-$$

where $R_1$, $R_2$, $R_3$, $R_4$ are the alkyl substituents, in which the sum of the number of carbon atoms is equal to or larger than 8 but smaller than 45; and, (b) The article is removed from the aqueous reaction solution and excess of tetraalkylammonium hydroxide is removed from the polymer surface by washing the polymer with a liquid miscible with the tetraallylammonium hydroxide.

DETAILED DESCRIPTION OF THE PRESENT INVENTION

The quaternary ammonium hydroxide with alkyl substituents having an overall number of carbon atoms between 8 and 45 (or "Quat" for short; $Q^+OH^-$) is able to react in presence of water with ester, amide, amidine or nitrile groups present in the acrylic and methacrylic substrate polymers, to yield Quat salts of acrylic or methacrylic acid:

—COOR+$Q^+OH^-$=>—COO$^-Q^+$+ROH

—CONHR+$Q^+OH^-$=>—COO$^-Q^+$+$RNH_2$

—CNHNHR+$Q^+OH^-$HOH=>—COO$^-Q^+$+$RNH_2$+$NH_3$

—CN+$Q^+OH^-$+HOH=>—COO$^-Q^+$+$NH_3$

The acrylate and methacrylate derivatives on the polymer surface are converted into the Quat salt of acrylic and methacrylic acids, respectively. The resulting carboxylates are carriers of negative charges and are highly hydrated under the physiological conditions. The carboxylate groups introduced by the process according to this invention cannot be removed by hydrolytic reactions. Because of its size and large hydrophobic substituents, Quat is not able to penetrate quickly and deeply into the hydrogel structure and the reaction is thereby confined to the surface region. Consequently, a continuous layer with a high concentration of carboxylate groups is formed without any significant migration or reaction to the bulk properties of the polymers. It is advisable to remove any residual Quat by a thorough washing with a liquid miscible with the particular Quat used in the reaction. The carboxylate groups formed in the reaction have quaternary amine counter-cations which cannot be removed by mere washing. Quaternary amines are known for their cytotoxicity and bactericidal properties. This is a potential advantage because it can prevent bacterial contamination of the product during its manufacture, storage and handling. This can decrease the bioburden and pyrogenicity of the product. For implants and other medical devices, it is often preferable to remove the Quat cation prior to use either by washing with an acid, or by a direct exchange of the Quat cation for a less toxic cation such as sodium, potassium or ammonium cations. The acid used in the washing should have pk value lower than 4.5 and advantageously below 3.5. Examples of suitable acids are phosphoric acid; hydrochloric acid; formic acid; citric acid and acetic acid. Furthermore, any implantable device should be equilibrated against an isotonic physiological solution prior to its use.

The main advantage of the reaction with Quats is the formation of a very thin, smooth, continuous surface layer possessing biomimetic properties. The thickness of the layer varies from about 0.1 microns to about 500 microns. If the layer is thinner than about 0.1 microns then it is difficult to ascertain its presence and continuity. Layers thicker than about 500 microns are sensitive to damage and have a distorted surface. The preferred layer thickness is between about 5 and 200 microns.

Since the reaction which forms the biomimetic layer is controlled by the diffusion of the reagent, a gradient of composition is created. This gradient spans from the unconverted material beneath the biomimetic layer, to the surface of the biomimetic layer which reaches maximum reaction conversion.

Most importantly, the reaction removes any hydrophobic domains from the surface so that the surface is fully hydrated, leaving no locations for strong non-specific protein adsorption. Another potential advantage is the formation of a well defined gradient with a negatively charged, completely wettable surface. Since the outermost surface layer is anchored on the less swellable layer underneath, the polymer in the surface is underswollen due to its confinement. If the surface is pitted, porous, scratched or otherwise damaged, the hydrolyzed polymer expands into the free space (a micropore, a tiny crack) and fills it with negatively charged hydrogel. It is believed this feature makes the layers according to the invention resistant to incrustations and calcifications and more resistant to bacterial colonization. In addition, such a layer is difficult to remove by erosion and relatively resistant to mechanical damage (it is "self-healing"). These features cannot be achieved by hydrophilic coatings, copolymerization with methacrylic acid, bulk hydrolysis, grafting with polymethacrylic acid or by other alternative methods.

An additional advantage of the layer formed by the method according to the invention is decreased wet friction and resistance against adhesion of gas bubbles, lipid particles, platelets and cells.

It is believed that excellent control of the reaction is achieved due to a combination of the large size of Quat, its partly hydrophobic character and by the fact that Quat is bound by the carboxylate formed by the reaction. (The Quat is a catalyst of hydrolysis that is "consumed" by the ionic reaction with the product.)

Because of the hydrophobic character of Quat, it can preferentially penetrate hydrophobic domains. This helps to self-regulate the formation of a uniform hydrophilic layer even on hydrophobic substrates, such as on methylmelhacrylate, acrylonitrile, methacrylonitrile, benzylacrylate, n-hexylmethacrylate or n-butylacrylate polymers. The quality and evenness of the layer is documented by the fact that lens surfaces can be treated according to our invention without any change in refractive power or resolution.

For the Quat to function correctly it is important to balance its reactivity, permeability and solubility in water. While its permeability decreases with an increasing number of carbon atoms in its substituents (limiting penetration into the bulk), its reactivity decreases (lowering the rate of hydrolysis). Sufficiently high reactivity and low permeability is achieved if the carbon atom number is between 8 and 45, but preferably between 15 and 24. Suitable quaternary amine hydroxides include dimethyldi-n-butyl ammonium hydroxide; tetra-n-propylammonium hydroxide; tetra-n-butylammonium hydroxide; trimethyloctadecylammonium hydroxide; tetraoctylammonium hydroxide; tetra-n-decylammonium hydroxide and other compounds from this class. Particularly suitable is tetra-n-butylammonium hydroxide with a good balance of reactivity, permeability and solubility. Mixtures of two or more different tetraalkylammonium hydroxides can be used for better control of the gradient.

Reaction is achieved by using aqueous solutions of Quats, typically in concentrations between 1% and 40% and, advantageously between 5% and 15% by weight. The reaction may be performed at any temperature at which the polymer and reaction solution are not physically hindered, e.g. freezing, melting, boiling, deforming. However, preferred reaction temperatures are between ambient (approximately 200° C. ) and 125° C., advantageously between 50° C. and 100° C. The concentrations and temperatures are selected to achieve reasonable reaction times, usually between 10 seconds and 6 hours but preferably between 1 and 60 minutes. Reaction time necessary to form the optimum layer depends on many variables and will be predetermined for each case by simple trial and error.

The process according to the present invention can be carried-out in several variants. In the variant described above, the polymer surface is contacted with an aqueous solution of the Quat for a predetermined time, then the excess Quat is removed by washing.

Another variant uses the Quat dissolved or dispersed in an organic solvent immiscible with water. The Quat solution/suspension is brought into contact with the hydrogel swollen with water. The Quat diffuses from the organic phase into the water-swollen hydrogel and the reaction proceeds on the hydrogel surface.

Still another variant uses Quat dissolved in a mixture of water and a suitable solvent, such as dimethylsulfoxide, sodium thiocyanate, glycerol, 1,2-propylene glycol, polyethylene oxide, etc. The solvent can facilitate the surface reaction of less reactive substrates (e.g., polymethylmethacrylate), to modify swelling of the surface layer, etc. Solvents with OH groups can become attached to the acrylate or methacrylate polymer by a transesterification reaction and act as a crosslinker or permanent plasticizer of the surface layer.

Many Quats are commercially available, others can be prepared from quaternary salts by known methods. For instance, it is possible to react tetraalkylammonium halides with silver oxide, or tetraalkylarnmonium sulfates with barium hydroxide, to yield tetraalkylammonium hydroxides. It is sometimes advantageous to form the Quat in situ by contacting the polymer with a solution of a tetraalkylammonium salt from which the Quat is generated by adding a suitable coreagent.

Substrates for the reaction are polymeric acrylates and methacrylates with hydrolyzable groups, including esters, amides, amidines and nitrites. The substrates are preferably hydrogels from acrylates and methacrylates containing hydrophilic functional groups, such as 2-ethoxyester; 1-glyceryl ester; 2 -hydroxyethylethoxyester; amide; 2-hydroxyethylamide; isopropylamide; amidine; or other known hydrophilic derivatives of acrylic or methacrylic acid.

The polymeric substrate can also contain polymeric acrylates and methacrylates with hydrolyzable hydrophobic functional groups, including nitrites or esters and amides with the following substituents: alkyl of C1 to C18; cycloalkyl; benzyl; benzophenoyl; hydroxybenzophenoyl and isobornyl.

Various hydrophobic and hydrophilic acrylates and methacrylates can be combined in one polymer chain, forming copolymers that are random, block or grafted copolymers. Combinations satisfying various practical requirements are numerous and well known to those skilled in the art. Acrylic or methacrylic monomers can be also combined with a minor concentration of other comonomers, such as ethylene, styrene, vinyl acetate and maleic anhydride. The concentration of such comonomers should be below 35% molar, and preferably less than 20% molar.

The acrylic or methacrylic polymer substrates can be covalently crosslinked by various methods well known per se. Crosslinked polymers, such as hydrogels, can be used for fabrication of various devices such as shunts; implants; lenses; wound covers; catheters; stents; etc.

Those polymer compositions that are insoluble in water can be also used as uncrosslinked substrates. Such compositions are often suitable for coatings on materials such as hydrophobic plastics, rubbers, metals, ceramics, etc. Coatings of acrylate or methacrylate polymers can then be treated by Quat according to the invention to impart biomimetic properties to the surface. The ability to form a gradient on a thin coating is a unique and very useful advantage of our invention. Other methods of hydrolysis (such as hydrolysis catalyzed by sodium hydroxide or sulfuric acid) cannot be controlled well enough to be useful for hydrophilization of thin layers.

Our invention is further illustrated by the following non-limiting examples (unless stated otherwise, all concentrations are in % by weight):

EXAMPLE 1

An intraocular hydrogel lens which is composed of 84.6% by weight 2-hydroxyethyl methacrylate (HEMA), 15% by weight methacryloyloxybenzophenone (MOBP) and 0.4% by weight ethyleneglycoldimethacrylate was cast in a polypropylene mold using 0.05% of isopropylpercarbonate as the initiator. The finished lens was washed and equilibrated in deionized water. The hydrated lens containing approximately 22.5% by weight of water was then contacted with a 10% solution of tetra-n-butylammonium hydroxide for 20 minutes at 85° C. The lens was then washed with 3% acetic acid and equilibrated in a buffered isotonic solution at pH 6.5.

The lens was noticeably more lubricious and more readily wettable with water after the treatment. Staining with the carboxylate-specific stain ruthenium red revealed that the lens surface was covered by a smooth, continuous, highly carboxylated layer while the lens interior was devoid of carboxylate. The thickness of the carboxylated layer was estimated to be 15 to 25 microns. The surface layer is resistant to damage by deformation of the lens (e.g., folding) or by the usual handling with forceps or gloved hands. The layer can withstand multiple autoclaving in isotonic saline without any adverse change. Optical resolution, clarity, weight and linear dimensions of the lens are unchanged by the treatment. The hydrated lens surface is resistant to adsorption of proteins, such as albumin. Tissue cells do not attach to and spread on the surface. If implanted, the surface does not elicit an inflammatory reaction and is not colonized by cells. If implanted into an eye, the lens stays clear without any visible protein deposits or cell attachment.

EXAMPLE 2

A capillary drain with tubular pores 125 microns in diameter is made from Poly(2-hydroxyethyl methacrylate) (PHEMA) hydrogel and dried at 120° C. for several hours. The PHEMA drain is placed into an evacuated flask equipped with a bottom inlet and heated to 110° C. A mixture of 1% by weight tetra-n-propylammonium hydroxide, 5% by weight tetra-n-decylammonium hydroxide, 10% by weight water and 84% by weight glycerol is heated to 110° C. and injected into the evacuated flask by the bottom inlet. Pressure in the flask is then increased to ambient assuring that pores are completely and quickly filled with the reactive mixture. The reaction is allowed to proceed for 5 minutes, then the reaction mixture is drained and replaced with water. After swelling and washing in 3% acetic acid for 24 hours, the drain is washed with water and equilibrated in a buffered isotonic solution at pH 7.5.

Staining with the carboxylate-specific stain ruthenium red revealed that the inner pore surface is covered by a smooth, continuous, highly carboxylated layer. The thickness of the carboxylated layer was estimated to be 2 to 5 microns. The drain has highly wettable pores and is intended as an implant assuring a permanent drainage of selected spaces inside the body. Contrary to some other capillary drains, the drain is resistant to clotting due to protein adsorption from plasma and deposition of cells on the surface.

EXAMPLE 3

A solid rod of a hydrogel containing 90% water by weight is made by the hydrolysis of polyacrylonitrile by NaOH in a NaSCN solution, by the subsequent coagulation of the polymer solution, and by washing and equilibrating the hydrogel in 0.9% by weight NaCl in water. The hydrolysis resulted in a copolymer containing nitrile, amide, amidine and carboxylate groups. The hydrogel rod is dried at 100° C. to a constant weight. The xerogel rod is contacted with a solution of aqueous 15% tetra-n-octylammonium hydroxide for 60 minutes at 90° C. The rod is then washed in 0.5% HCl, in deionized water, and 1% NaHCO$_3$. The hydrogel is then dried at an elevated temperature.

The modified hydrogel rod has a highly lubricous surface layer with improved biocompatibility and resistance to foreign body reaction and calcification upon implantation. The surface is free of nitrile, amide or amidine groups. The xerogel rod is intended to serve as an osmotic tissue expander.

EXAMPLE 4

A polyacrylonitrile fiber is prepared by spinning of polyacrylonitrile solution in a concentrated zinc chloride solution into an aqueous coagulating bath, washed and dried. The fiber with a diameter of 50 microns is immersed in a solution of 15% by weight tetraethylammonium hydroxide dissolved in an aqueous solution of 42.5% NaSCN. NaSCN is added as a polyacrylonitrile solvent to promote its swelling. The fibers are treated for 5 minutes at 50° C., then thoroughly washed in water and dried.

The fiber surface is covered by a very thin carboxylated layer (several microns thick) with a distinct concentration gradient detectable by staining with ruthenium red. The fibers have improved surface wettability, do not attract or entrap gas bubbles, clot, proteins, platelets or blood cells and can be used for construction of blood filters.

EXAMPLE 5

A stainless steel sheet is thoroughly cleaned with a 1% phosphoric acid solution, then washed with deionized water and dried. The sheet is then coated with a solution of a random copolymer composed of 65% by weight 2-ethylhexylacrylate and 35% by weight ethylacrylate. The coating is dried at ambient temperature. The dry coating is approximately 150 microns thick. The coated sheet is contacted with an 10% solution of aqueous cetyltrimethylammonium hydroxide for 5 hours at 20° C. and washed with deionized water and dried. If contacted with water, the sheet becomes lubricious and readily wettable with water.

Staining with the carboxylate-specific stain ruthenium red revealed a smooth, continuous, highly carboxylated layer approximately 5 to 15 microns thick. If submersed in ambient water for an extended period of time, the surface stays clean, free of biofilm or other deposits while other surfaces nearby are covered by a slimy layer rich in bacteria of several kinds. No organisms are found attached to the hydrated surface. If left in dry state in ambient air for an extended period of time, the surface is found to be free of bacterial contamination. The coating is designed for medical instruments and processing equipment in pharmaceutical industry.

EXAMPLE 6

A guidewire made of Ni—Ti alloy is thoroughly cleaned with phosphoric acid and deionized water. The wire is then coated with a solution of a copolymer composed of 65% by weight n-butylmethacrylate, 5% by weight 2-hydroxyethylmethacrylate and 35% by weight ethylmethacrylate. The coating is dried at elevated temperature under vacuum. The dry coating is approximately 50 microns thick. The coated wire is contacted with a 30% solution of tetra-n-propylammonium hydroxide for 45 minutes at 40° C., After treatment the wire is washed in lo phosphoric acid, then washed with deionized water and equilibrated in physiological saline buffered to pH 7.2. The wire was dried and sterilized by gamma irradiation at the 2.5 megarad dose.

If contacted with water, the wire surface is readily wettable with water and hydrates quickly. Staining with the carboxylate-specific stain ruthenium red revealed a smooth, continuous, highly carboxylated layer approximately 3 to 5 microns thick. The hydrated, carboxylated surface of the wire is very lubricious and its wet friction is very low. The guidewire is used in blood vessels and its surface has an excellent resistance to clotting and adhesion of platelets. It does not stick to either vascular endothelium or to the walls of a catheter.

Obviously, numerous modifications and variations of the present invention are possible in light of the above teachings. It is therefore understood that within the scope of the appended claims, the invention may be practiced otherwise than as specifically described herein.

What is claimed is:

1. A method of creating a biomimetic negatively charged, hydrated layer on the surface of an article formed primarily from polymers selected from acrylic polymers, methacrylic polymers, and copolymers or mixtures thereof, which polymers are hydrogel polymers which are capable of being swelled in water, which comprises:

(a) contacting said article at a temperature between 20° C. and 125° C., with tetraalkylammonium hydroxide solution of a solvent which is immiscible with water, said solution having at least one tetraalkylammonium hydroxide having a general formula:

$$R_1R_2R_3R_4N^+OH^-$$

where $R_1$, $R_2$, $R_3$, $R_4$ are alkyl substituents, in which the sum of the number of carbon atoms is equal to or larger than 8 but less than 45, and;

(b) removing the article from said tetraalkylammonium hydroxide solution and removing the excess of the said solution by washing in an aqueous washing solution of an acid with a pK value of less than 4.5, said aqueous washing solution being miscible with said tetraalkylammonium hydroxide.

2. The method according to claim 1 wherein said tetraalkylammonium hydroxide has at least 15 but less than 25 carbon atoms.

3. The method according to claim 1 wherein said step (a) solution contains from 1% by weight to 40% by weight of said tetraalkylammonium hydroxide.

4. The method according to claim 3 wherein said solution contains from 5% by weight to 15% by weight of said tetraalkylammonium hydroxide.

5. The method according to claim 1 wherein said temperature is between 50° C. and 90° C.

6. The method according to claim 1 wherein said polymers are selected from polymers having ester pendant groups, polymers having amide pendant groups, polymers having nitrile pendant groups and copolymers and mixtures thereof.

7. The method according to claim 6 wherein said amide pendant groups are derived from amides of compounds selected from the group consisting of ammonia; an alkylamine containing 1 to 4 carbons; a dialkylamine containing 2 to 8 carbons; hydroxyalkylamine containing 2 to 6 carbons; glucosamine; arginine; lysine; taurine and alanine.

8. The method according to claim 6 wherein said esters are esters of hydroxy compounds selected from the group consisting of ethylene glycol; diethylene glycol; triethylene glycol; glycerol; 1,2-propylene glycol; benzylalcohol; dihydroxybenzophenone; borneol; isoborneol and aliphatic alcohols containing between 1 and 8 carbon atoms.

9. The article having a product comprising a surface polymer layer created by the method according to claim 1.

10. A method of creating a biomimetic negatively charged, hydrated layer on the surface of an article formed primarily from polymers selected from acrylic polymers, methacrylic polymers, and copolymers or mixtures thereof, which polymers are hydrogel polymers which are capable of being swelled in water, which comprises:

(a) contacting said article at a temperature between 20° C. and 125° C., with tetraalkylammonium hydroxide aqueous solution, said solution having at least one tetraalkylammonium hydroxide having a general formula:

$$R_1R_2R_3R_4N^+OH^-$$

where $R_1$, $R_2$, $R_3$, $R_4$ are alkyl substituents, in which the sum of the number of carbon atoms is equal to or larger than 8 but less than 45, and;

(b) removing the article from said tetraalkylammonium hydroxide solution and removing the excess of the said solution by washing in a washing liquid miscible with said tetraalkylammonium hydroxide.

11. The method according claim 10 wherein said tetraalkylammonium hydroxide has at least 15 but less than 25 carbon atoms.

12. The method according to claim 10 wherein said step (a) aqueous solution is an aqueous solution containing said tetraalkylammonium hydroxide, water, and a water-miscible solvent.

13. The method according to claim 12 wherein said water-miscible solvent is a compound selected from the group consisting of dimethylsulfoxide; dimethylformamide; y-butyrolactone; tetrahydrofuran; dioxane; sodium thiocyanate; glycerol; propylene glycol; ethylene glycol; hydroxyalkyl amine where the alkyl substituent has 2 to 6 carbons; diethylene glycol; triethylene glycol; polyethylene glycol; methylethers of polyethylene glycols; and copolymers of ethylene and propylene glycols.

14. The method according to claim 10 wherein said step (a) solution contains from 1% by weight to 40% by weight of said tetraalkylammonium hydroxide.

15. The method according to claim 14 wherein said solution contains from 5% by weight to 15% by weight of said tetraalkylammonium hydroxide.

16. The method according to claim 10 wherein said temperature is between 50° C. and 90° C.

17. The method according to claim 10 wherein said polymers are selected from polymers having ester pendant groups, polymers having amide pendant groups, polymers having nitrile pendant groups and copolymers and mixtures thereof.

18. The method according to claim 10 wherein said step (b) is an aqueous washing solution of an acid with pK value of less than 4.5.

19. The method according to claim 17 wherein said esters are esters of hydroxy compounds selected from the group consisting of ethylene glycol; diethylene glycol; triethylene glycol; glycerol; 1,2-propylene glycol; benzylalcohol; dihydroxybenzophenone; borneol; isoborneol and aliphatic alcohols containing between 1 and 8 carbon atoms.

20. The article having a product comprising a surface polymer layer created by the method according to claim 10.

* * * * *